US011361849B2

(12) United States Patent
Deng et al.

(10) Patent No.: US 11,361,849 B2
(45) Date of Patent: Jun. 14, 2022

(54) HIERARCHICAL SELF-LEARNING SYSTEM FOR COMPUTERIZED CLINICAL DIAGNOSTIC SUPPORT

(71) Applicant: KONINKLIJKE PHILIPS N.V., Eindhoven (NL)

(72) Inventors: Yinhui Deng, Shanghai (CN); Xiaomin Li, Shanghai (CN); Xiaolin Gu, Shanghai (CN); Vijay Thakur Shamdasani, Kenmore, WA (US); Ying Wu, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1296 days.

(21) Appl. No.: 15/030,705

(22) PCT Filed: Nov. 10, 2014

(86) PCT No.: PCT/IB2014/065921
§ 371 (c)(1),
(2) Date: Apr. 20, 2016

(87) PCT Pub. No.: WO2015/071815
PCT Pub. Date: May 21, 2015

(65) Prior Publication Data
US 2016/0283680 A1    Sep. 29, 2016

Related U.S. Application Data

(60) Provisional application No. 61/903,475, filed on Nov. 13, 2013.

(51) Int. Cl.
*G16H 10/60*   (2018.01)
*G16H 50/20*   (2018.01)
(Continued)

(52) U.S. Cl.
CPC ............. *G16H 10/60* (2018.01); *G06N 20/00* (2019.01); *G16H 50/20* (2018.01); *G16H 70/20* (2018.01)

(58) Field of Classification Search
None
See application file for complete search history.

(56) References Cited

U.S. PATENT DOCUMENTS 5,622,171 A    4/1997 Asada et al.
2005/0216208 A1   9/2005 Saito et al.
(Continued)

FOREIGN PATENT DOCUMENTS

WO    2004072858 A1   6/2006

OTHER PUBLICATIONS

Junghoe Kim, Vince D. Calhoun, Eunsoo Shim, Jong-Hwan Lee, "Deep neural network with weight sparsity control and pre-training extracts hierarchical features and enhances classification performance:" NeuroImage, 2016,vol. 124, Part A, pp. 127-146, https://doi.org/10.1016/j.neuroimage.20 (Year: 2016).*

*Primary Examiner* — Rachel L. Porter

(57) ABSTRACT

Individual computer diagnostic support (CDS) systems are coupled to a 'global' CDS system, each of the CDS systems using the same learning system or the same learning system technique. Training and testing cases from each of the individual CDS systems are provided to the global CDS system, and the global CDS system uses these training cases to produce learning system parameters based on the training cases. Having more training cases than any of the individual CDS systems, the parameters provided by the global CDS system offer a higher quality diagnostic output than any of the individual CDS systems. The learning system parameters at the global CDS system may be provided to each of the individual CDS systems, to update the parameters of the (Continued)

individual CDS systems' learning system. The global CDS may also refine and/or adjust the structure of the embodied learning systems.

11 Claims, 5 Drawing Sheets

(51) Int. Cl.
*G06N 20/00* (2019.01)
*G16H 70/20* (2018.01)

(56) References Cited

U.S. PATENT DOCUMENTS

| | | | |
|---|---|---|---|
| 2006/0184475 A1* | 8/2006 | Krishnan | G16H 10/60 |
| | | | 706/20 |
| 2008/0059392 A1* | 3/2008 | Barnhill | G06N 20/10 |
| | | | 706/13 |
| 2011/0119212 A1* | 5/2011 | De Bruin | G16H 50/70 |
| | | | 706/12 |
| 2012/0109689 A1 | 5/2012 | Lee | |
| 2012/0150555 A1 | 6/2012 | Truyen et al. | |
| 2013/0138454 A1 | 5/2013 | Van Zon et al. | |
| 2013/0174084 A1 | 7/2013 | Lord et al. | |
| 2014/0343957 A1* | 11/2014 | Dejori | G16H 50/20 |
| | | | 705/2 |
| 2015/0058322 A1 | 2/2015 | Dimitrova et al. | |

\* cited by examiner

HIERARCHICAL SELF-LEARNING SYSTEM FOR COMPUTERIZED CLINICAL DIAGNOSTIC SUPPORT

CROSS-REFERENCE TO PRIOR APPLICATIONS

This application is the U.S. National Phase application under 35 U.S.C. § 371 of International Application No. PCT/IB2014/065921, filed on Nov. 10, 2014, which claims the benefit of U.S. Provisional Application No. 61/903,475, filed on Nov. 13, 2013. These applications are hereby incorporated by reference herein.

FIELD OF THE INVENTION

This invention relates to the field of medical diagnostics, and in particular to a computer-based self-learning system that includes multiple diagnostic systems arranged in a hierarchical manner.

BACKGROUND OF THE INVENTION

Clinical diagnostic support (CDS) systems are commonly used to aid a medical practitioner in the diagnostic process. A CDS system may be deployed at a doctor's office, a clinic, a health center, and so on. The users of the system provide input data to the CDS regarding a patient, such as the patient's vital signs, the results of lab tests, observations, background, family history, and so on; and the CDS attempts to determine whether this data is consistent with a particular medical condition, or a set of medical conditions. This determination may be presented to the practitioner as binary, yes/no determinations, a set of likelihood values, and so on.

Most CDS systems are embodied as self-learning, or 'machine learning' systems that improve the accuracy of their diagnostics by receiving feedback on the accuracy of each diagnosis, or by being 'trained' using a set of example cases. That is, the 'correct' diagnosis is provided in addition to the input data, and the system processes the data in light of the correct diagnosis to increase the likelihood of providing the correct diagnosis when a similar set of input data is provided for another patient. Having the 'correct' diagnosis also allows for testing of the learning system to assess its performance and/or to determine whether the system is robust enough for use in actual clinical applications.

The learning system may be embodied using any of a variety of machine learning techniques, including neural networks, transductive and Bayesian inference, decision-tree learning, and so on. In each of these techniques, the learning system includes a process for adjusting a set of parameters associated with the learning process during the training or feedback stage, and a process that applies these parameters to the input data to produce a diagnostic result. For example, a neural network comprises a plurality of internal nodes that are coupled to each input, to each other, and to the output(s). Parameters are associated with each node and each connection between the nodes that define how a given set of input values are propagated through the network to provide an output value at the output(s). During the training phase, the parameters are adjusted based on a difference between the determined output value and a known, 'correct' output value to reduce the difference, thereby increasing the likelihood of producing the known, 'correct' output(s) when applied to a subsequent set of input data.

The number of example cases needed to train the learning system is dependent upon the technique used, the inherent correlation between the input data and the output, the variance among the training cases, and so on. In robust trainable systems, the accuracy of the learning system's diagnoses will increase as the number of training cases increases. However, the number of cases that any particular doctor, clinic, or medical center, may be able to provide will generally be relatively low, particularly for cases that are to be used for training and testing the CDS with known 'correct' diagnoses.

Additionally, the determination of the 'correct' diagnosis may vary with the diagnostic skill(s) of the user(s) of the CDS, and in some embodiments, the particular CDS may be trained to merely reinforce the user's mistaken diagnoses.

SUMMARY OF THE INVENTION

It would be advantageous to provide a computer diagnostic system (CDS) that is less dependent upon the particular users/trainers of the CDS.

To better address this concern, in an embodiment of this invention, individual computer diagnostic support (CDS) systems are coupled to a 'global' CDS system, each of the CDS systems using the same learning system or the same learning system technique. Training and testing cases from each of the individual CDS systems are provided to the global CDS system periodically, or aperiodically, and the global CDS system uses the training cases from the variety of individual CDS systems to produce learning system parameters based on the training cases. Having more training cases than any of the individual CDS systems, the parameters provided by the global CDS system offer a higher quality diagnostic output than any of the individual CDS systems. When testing reveals an improvement in the accuracy or robustness of the global CDS system, the learning system parameters at the global CDS system may be provided to each of the individual CDS systems, to update the parameters of the individual CDS systems' learning system. The global CDS may also refine and/or adjust the structure of the embodied learning systems to further improve the accuracy, robustness, and/or efficiency of these learning systems.

BRIEF DESCRIPTION OF THE DRAWINGS

The invention is explained in further detail, and by way of example, with reference to the accompanying drawings wherein.

Throughout the drawings, the same reference numerals indicate similar or corresponding features or functions. The drawings are included for illustrative purposes and are not intended to limit the scope of the invention.

DETAILED DESCRIPTION

In the following description, for purposes of explanation rather than limitation, specific details are set forth such as the particular architecture, interfaces, techniques, etc., in order to provide a thorough understanding of the concepts of the invention. However, it will be apparent to those skilled in the art that the present invention may be practiced in other embodiments, which depart from these specific details. In like manner, the text of this description is directed to the example embodiments as illustrated in the Figures, and is not intended to limit the claimed invention beyond the limits expressly included in the claims. For purposes of simplicity and clarity, detailed descriptions of well-known devices, circuits, and methods are omitted so as not to obscure the description of the present invention with unnecessary detail.

FIGS. 1A-1D illustrate example operations associated with a prior art clinical diagnostic support (CDS) system 150.

Figure 1A:
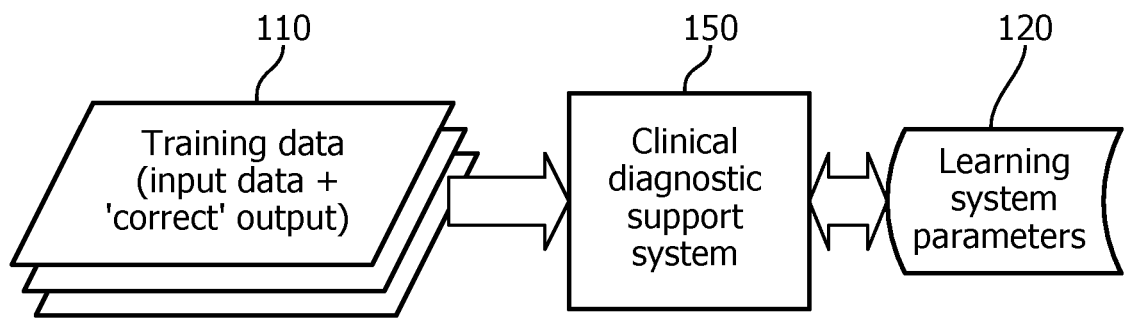
FIGS. 1A-1D illustrate example operations associated with a prior art clinical diagnostic support system.

FIG. 1A illustrates an example training of the learning system within the CDS system 150. A plurality of training data 110 is provided to the CDS system 150. This training data 110 includes a plurality of input data associated with a patient (actual or hypothetical), and may include, for example, the patient's vital signs, results of lab tests, observations, symptoms, and so on, as well as background information, such as gender, age, ethnic background, family history, and the like. In some embodiments, the set of input data provided is specific to the particular illness or disease that is the target of the diagnostics. For example, family history may be provided for diseases that are known to be genetic, but not for other diseases. The input data 110 may not correspond directly to the 'raw data' that is collected, but may be the result of a preprocessing of such raw data. For example, often the ratio between two elements in the raw data may be known to have better diagnostic value than each of the values of the elements, and this ratio may be provided as the input data.

The CDS system 150 may be configured to address a particular illness or disease, or a set of illnesses and/or diseases, to provide an identification of one or more illnesses or diseases that are consistent with the input data and/or an identification of one or more illnesses or diseases that are inconsistent with the input data. The CDS system 150 includes a learning system that is configured to receive the input data and provide a diagnostic output. The quality or accuracy of the CDS system 150 is assessed based on whether the provided diagnostic output is correct, and/or the degree to which the output is correct.

The "correctness" of the diagnostic output is determined by comparing the diagnostic output with a known, or assumed 'correct' diagnosis. The 'correct' diagnosis may be a diagnosis that is provided by a medical practitioner upon review of the same input data, or by a subsequent development in the patient's condition. For example, if the diagnostic output is that the patient is likely experiencing the initial stages of a particular disease, and the patient eventually experiences the later stages of this disease, the diagnostic output is determined to have been correct; if the patient does not exhibit the later stages of the disease, the diagnostic output is determined to have been incorrect.

To improve the accuracy of the CDS system 150, sets of input data for which a 'correct' diagnosis is available are provided to the learning system within the CDS system 150 while in the 'learning mode' illustrated in FIG. 1A. Both the input data and the 'correct' diagnosis are provided to the learning system, and the learning system processes this input data and 'correct' diagnosis to increase the likelihood that the diagnostic output from the CDS system 150 is consistent with this 'correct' diagnosis.

As noted above, a learning system is characterized by the parameters 120 that determine how the diagnostic output is affected by each element of the input data, or sets of elements of the input data. For ease of presentation and understanding, the paradigm of a learning system that uses a neural network comprising multiple layers of single-output nodes with connections between the nodes of each adjacent layer is used. The input data is connected to the first layer, and the diagnostic output is produced at the last layer. Each node has a 'bias', or 'threshold' parameter, and each connection between nodes has a 'weight' parameter. The output of each node is propagated to the nodes of the next layer by multiplying the output of the node by the weight of each connection to each node at the next layer. Each node includes a transfer function that combines the inputs to the nodes and the node's bias to produce that node's output. A sigmoid function is commonly used as the transfer function at each node.

In this example embodiment, the output value of each output's node is compared to the aforementioned known or assumed 'correct' value for that output to produce an error value. The parameters (bias and weight) of the nodes and connections define the effect that each input and intervening node had on the output value, and correspondingly, the error value. These parameters are adjusted based on the differential or gradient of the error with respect to each parameter and a 'learning rate'. In a multi-output learning system, the parameters may be adjusted to provide a minimum composite error (such as a 'mean squared error').

The learning rate determines how large the corrections to the parameters are, thereby defining the effect of each set of input data on the current state of the learning machine, defined by the prior values of the parameters. A low learning rate may require a large number of sets of input data to adequately train the learning system, whereas a high learning rate requires fewer sets of input data, but may introduce abrupt changes, and fail to achieve an adequate accuracy.

Figure 1B:
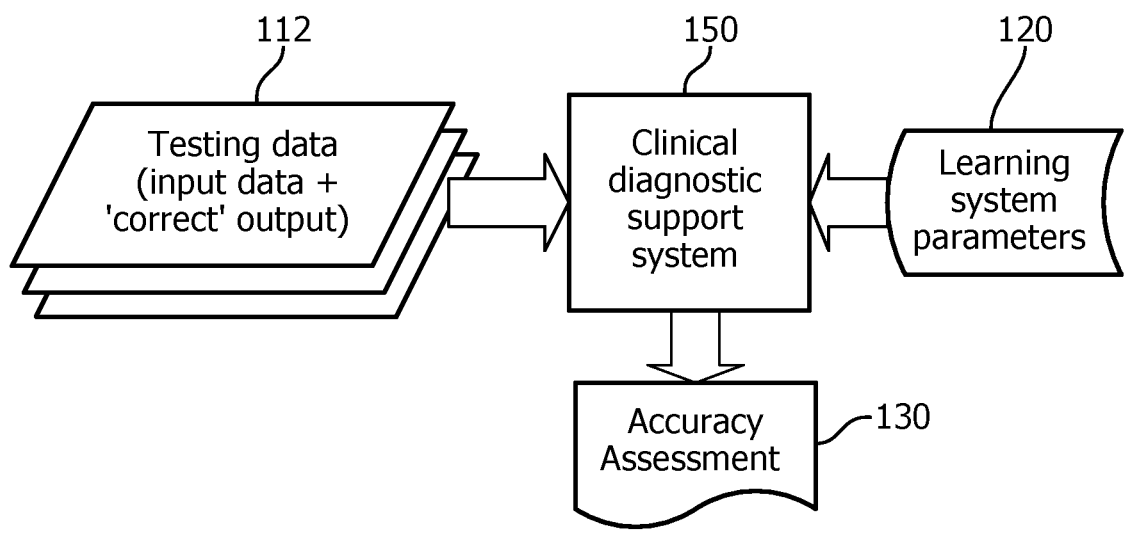

After all of the training data is processed, the learning system may be tested for accuracy as illustrated in FIG. 1B. Multiple sets 112 of input data and corresponding 'correct' diagnosis are provided to the CDS system 150, and the learning system within the CDS system 150 uses the learning system parameters 120 that were produced during the training stage of FIG. 1A.

The testing data 112 may include a subset of the training data 110 that was used to train the learning system, or it may be independent of the training data 110. In this case, however, the learning system parameters 120 are not adjusted based on the 'correct' diagnosis for each set of input data; instead, the output diagnostic is compared to the 'correct' diagnosis to provide an accuracy measure for each output diagnostic. The accuracy measures for each output diagnostic may be combined to provide one or more accuracy statistics associated with the quality of the CDS system 150 with these parameters 120. These statistics and other determinations may be presented in an accuracy assessment report 130. Based on such an accuracy assessment 130, a user may determine whether the CDS system 150 with the determined learning system parameters 120 is suitable for use in a clinical environment.

Figure 1C:
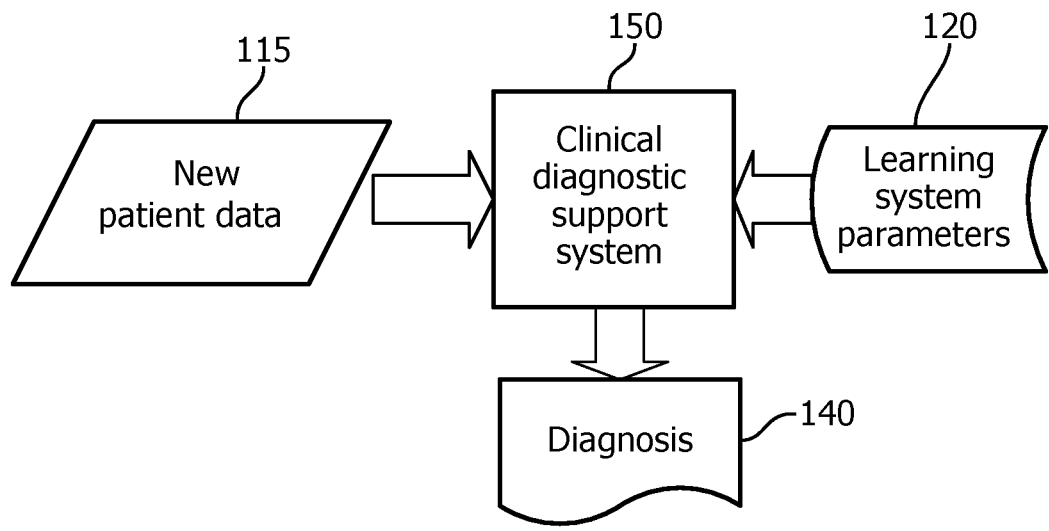

FIG. 1C illustrates an example CDS system 150 with the determined learning system parameters 120 being used to perform diagnoses of a new patient's input data 115, or an existing patient's updated input data. In this configuration the CDS system operates as it did in the testing stage of FIG. 1B to provide a diagnostic output 140 based on the input data 115 and the current parameters 120 of the learning system within the CDS system.

The diagnostic output 140 may be used by a medical practitioner to offer a prescription, request further testing, and so on. As noted above, however, the accuracy of this diagnostic output 140 is highly dependent upon the number of sets of training data 110, and the quality of the assumed 'correct' diagnosis for each set of training data 110.

Figure 1D:
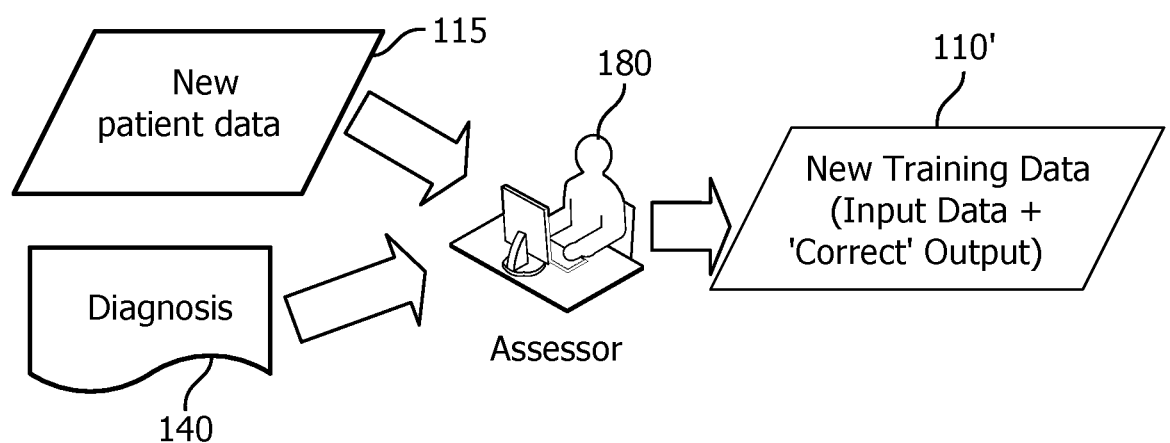

The number of sets of training data may be increased by determining the 'correct' diagnosis for an existing set of input data, as illustrated in FIG. 1D. This 'correct' diagnosis may be obtained, for example, by providing the input data 115 to an 'assessor' 180, such as a diagnostic expert in the field of the particular illness or diseases being addressed by the CDS system 150. As noted above, the 'correct' diagnosis may also be determined by subsequent developments in the patient's case. When a 'correct' diagnosis can be determined for a particular set of input data, this input data and 'correct' diagnosis may be used to provide a new set of training data 110'.

The creation of new training data, however, is still limited to the number of cases that have been provided to the CDS system 150, the availability of 'correct' diagnoses for these cases, and the quality/accuracy of these available diagnoses.

Figure 2:
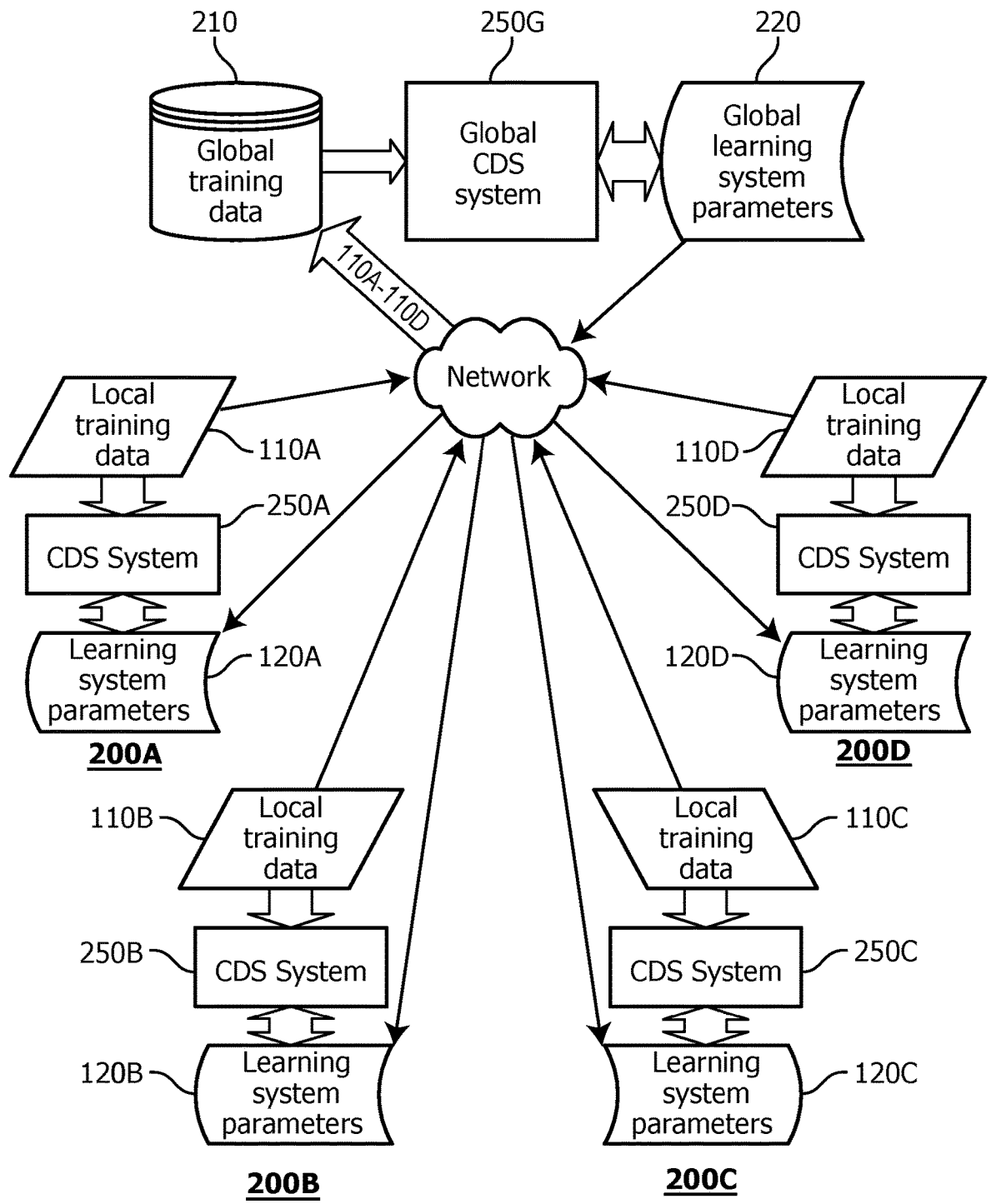
FIG. 2 illustrates an example network of clinical diagnostic support systems with a global CDS system in communication with local CDS systems.

FIG. 2 illustrates an example network of clinical diagnostic support systems with a global CDS system 250G is in communication with CDS systems 250A-250D at local CDS sites 200A-200D. This network is intended to provide a more robust and accurate set of training system parameter values than the parameter values that are conventionally available at any particular CDS site 200A-200D.

In this example embodiment, all of the CDS systems 250A-250D, 250G use a similar learning system, such that the learning system parameters 120A-120D, 220 are compatible with each other, or can be transformed to provide this compatibility. For ease of reference and understanding, the learning system within each of these systems 250A-250D, 250G is assumed hereinafter to be identical.

As noted above, a single CDS site 200A-200D has a limited amount of training data, and the quality of the 'correct' diagnoses used for training each CDS system 250A-250D may vary among each of the sites 200A-200D. In accordance with an aspect of this invention, the global CDS system 250G is configured to receive the training data from each of the sites 200A-200D, thereby accumulating more training data than any of the individual CDS systems 200A-200D may have access to. This large amount of training data will also minimize the effects of any particular erroneous 'correct' diagnosis in the training data.

The global CDS system 250G receives the local training data 110A-110D from the local CDS systems 200A-250D and stores this data as global training data 210. Any of a variety of techniques may be used to obtain the local training data 110A-110D. The local CDS systems 250A-250D may be configured to periodically or aperiodically contact the global CDS system 250G and upload any new training data, and/or, the global CDS system 250G may periodically or aperiodically contact each local CDS system 250A-250D and request an upload of any new training data. Other techniques may also be used to populate the global training data 210 with the training data 110A-110D. As noted above, if the CDS systems 250A-250D, 250G are not identical, the global CDS system 250G may pre-process the received training data as necessary to provide compatibility. Similarly, if the local CDS systems 250A-250D pre-process the patient data to provide, for example, ratios of elements in the patient data, this pre-processing will also be performed at the global CDS system 250G.

Upon receipt of new training data 210, the global CDS system 250G may use this new training data 210 to further train the learning system within the global CDS system 250G to produce a new set of global learning system parameters 220. Optionally, the operator of the global CDS system 250G may 'pre-screen' the received new training data before the changes to the global learning system parameters 220 are applied. For example, the operator may apply the new training data to the global CDS system 250G in the diagnostic mode, rather than the learning mode, to compare the diagnostic output of the CDS system 250G to the provided 'correct' diagnosis in the new training data 210. If a significant difference exists between the diagnostic output and the 'correct' diagnosis, the new training data 210 may be provided to a medical practitioner to assess whether the 'correct' diagnosis in the received training data is consistent with the corresponding input data. This pre-screening may be applied to all training data received, or to training data received from select CDS systems, based on an assumed quality and/or reliability associated with the diagnoses from each CDS system 200A-200D.

After processing the training data to create or modify the global learning system parameters 220, the global CDS system 250G with these parameters 220 is tested to provide the aforementioned accuracy assessment and/or accuracy statistics. If the testing indicates an acceptable level of accuracy and/or reliability, these parameters 220 are made available to the local CDS sites 200A-200D.

Presumably, because these updated parameters 220 are produced using additional training data, the accuracy and/or reliability of the CDS system 250G using the updated parameters 220 can be expected to be better than that of the CDS system 250G using the prior parameters, before the updating. Optionally, the operator of the global CDS system 250G may not provide these updated parameters if it can be determined that the updated parameters do not perform as well as the prior parameters. Because the results of the testing will be dependent upon the particular set of testing data applied, and other random factors, this determination regarding the performance of the updated parameter may include the use of one or more statistical tests to determine if the observed differences are 'significant' enough to withhold the release of these new learning system parameters 220.

The new learning system parameters 220 may be downloaded to the local CDS sites 200A-200D using any of a variety of techniques. The global CDS system 250G may notify each site 200A-200D that the new parameters 220 are available, and wait for a request for download from each site 200A-200D. Alternatively, the global CDS system 250G may 'broadcast' the new parameters 220 to all of the sites 200A-200D, for example, as an attachment to an e-mail.

Each site 200A-200D has the option of updating its local learning system parameters 120A-120D based on the new parameters 220, and may do so automatically, or after local testing. This updating may be a direct replacement of the local parameters 120 with the updated parameters 220, or it may include some preprocessing, depending on possible differences between the local CDS system and the global CDS system. For ease of reference, the terms 'update the parameters' and 'replace the parameters' are defined herein as a change to one or more of the parameters.

A site 200 may apply its own test data to its system 250 with the prior parameters 120, and subsequently with the new parameters 220 before replacing the prior parameters 120 with the new parameters 220. As remarked above, presumably the new parameters 220 will provide higher quality and/or reliability than the local parameters 120, but if it can be determined that the parameters 220 do not provide this higher quality and/or reliability, the operator of the site 200 may postpone the updating of the parameters 120 with the new parameters 220 until the cause of the poorer performance can be determined.

As noted above, the quality and/or reliability provided by a given set of parameters 120, 220 is dependent upon the accuracy of the 'correct' diagnosis provided in the training data. In like manner, the results of testing using local test data will be dependent upon the accuracy of the 'correct' diagnosis in the test data. If the new parameters 220 exhibit poorer performance than the local parameters 120, either the parameters 220 are truly poorer than the local parameters 120 when applied to the local test data, or the diagnoses provided in the test data is poorer than the diagnoses in the global training data 210 that was used to determine the parameters 220. The operator of the local site 200 may postpone updating of the parameters 120 with the new parameters 220 until it can be resolved which of these scenarios is present at the site 200.

In the general case, the global parameters 220, being based on a number of training cases that significantly exceeds the number of training cases available at a given site, will be superior to the local parameters 120, and each site 200A-200D will update its local parameters 120A-120D with a copy of the parameters 220. Thereafter, as the global parameters 220 are updated by an increasing number of training cases provided to the global CDS system 250G over time, the updated learning system parameters 220 will replace the prior copy of the parameters 220 as the local learning system parameters 120A-120D at each site.

Each of the local CDS sites 200A-200D may be independent of each other, and may not even know the identity of the other sites. The global CDS system 250G may be provided by the vendor of the local CDS systems 250A-250D, with the networking and parameter-updating capability being provided as a feature that distinguishes these CDS systems 250 from competing CDS systems.

That is, for example, purchasers of the CDS system 250 may be offered the opportunity to receive the learning system parameters 220 from the global CDS system 250G in return for providing their local training data 110A-110D to the global CDS system 250G. The local training data 110A-110D that is provided to the global CDS system 250G need not include an identification of the particular patient, thereby assuring the patient's privacy. Other security measures may also be used.

Figure 3A:
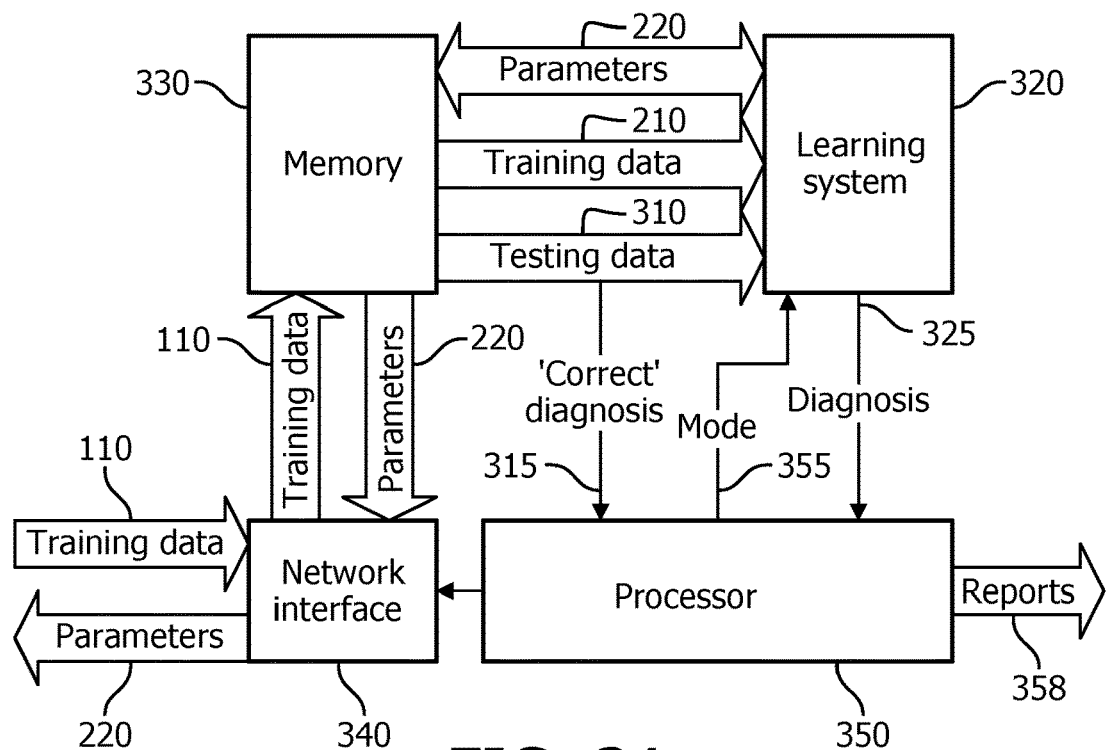
FIGS. 3A-3B illustrate example global and local clinical diagnostic support systems, respectively.
Figure 3B:
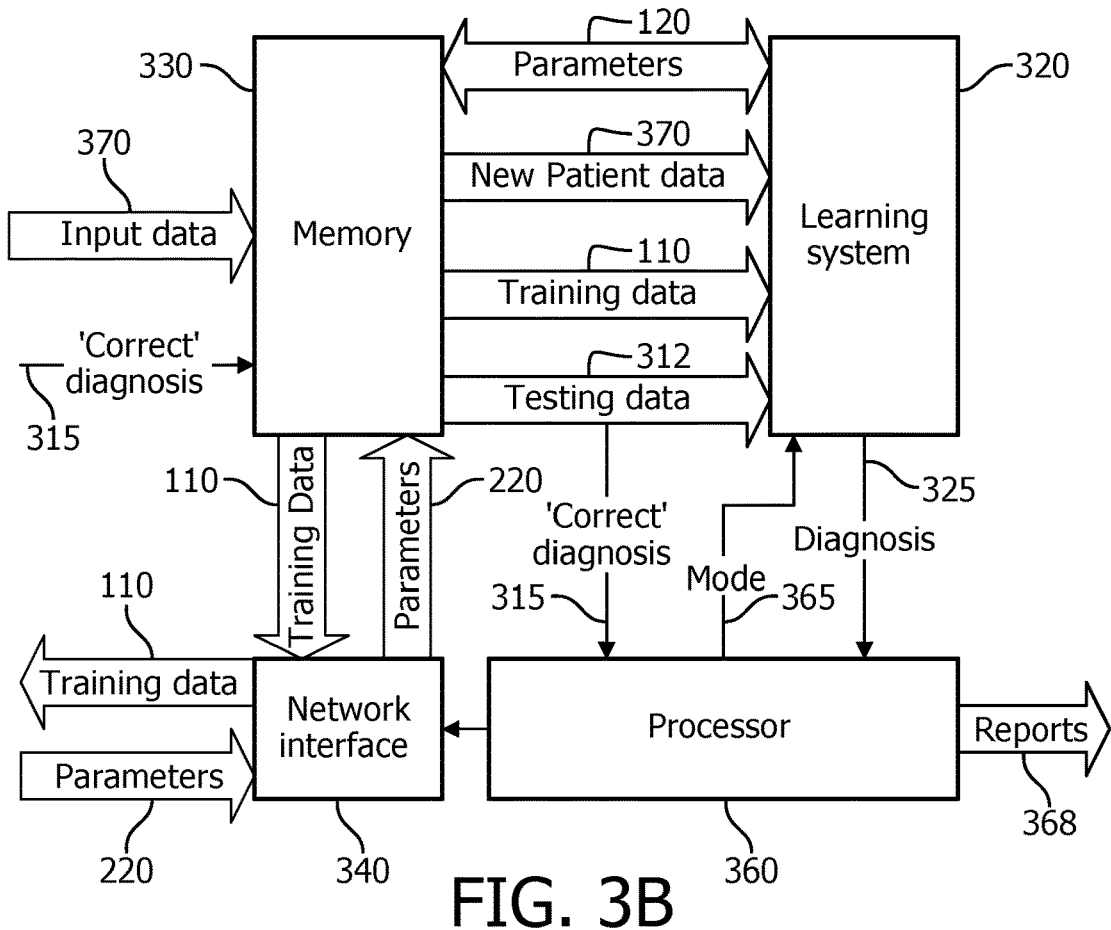

FIGS. 3A and 3B illustrate example global and local CDS systems, respectively. The example global CDS system of FIG. 3A includes a learning system 320, a memory 330, a network interface 340, and a processor 350 that controls the operation of the learning system 320 and network interface 340.

As discussed above, the network interface 340, which may be any communication device that can send and receive data to a plurality of local CDS systems, receives training data 110 from each of the plurality of local CDS systems and stores this data 110 as the collective global training data 210 in memory 330. The memory 330 also contains global learning system parameters 220. These parameter include structural and operational parameters that enable the learning system 320 to provide a diagnostic output 325 corresponding to a given set of input data corresponding to a patient. This patient may be an actual person, or a hypothetical person, such as a hypothetical person that has one specific disease, with hypothesized input data that is likely to be present in this hypothetical person. Such hypothetical patients may be used to initialize the learning system parameters by processing the hypothetical input data of each hypothetical patient and comparing the resultant diagnosis 325 to the specific disease of each hypothetical patient. The processing of hypothetical patients may also be used as a teaching tool for medical students.

In the example of a neural network based learning system, the structural parameters may be the structure of the network (number of inputs, number of outputs, number of hidden layers, the number of nodes at each layer, the connections between nodes, and so on), the assignment of elements of the input data to particular inputs of the network, the assignment of particular outputs of the network to the output diagnostic data, and so on. The operational parameters may be the aforementioned bias associated with each node and weight associated with each connection between the nodes.

To initialize the parameters 220, the processor 360 sets the learning system 320 into the learning mode via mode control 355, and sequentially provides the learning system with sets of training data (input data +'correct' diagnosis) 210. As each set of training data 210 is processed by the learning system 320, the learning system 320 compares its determined diagnosis to the 'correct' diagnosis and adjusts the parameters 220 to increase the likelihood that the determined diagnosis will more closely match the 'correct' diagnosis in subsequent iterations. In some learning systems, groups of sets of training data 210 may be processed before the parameters 220 are adjusted.

Depending upon the time required to process each set of training data 210, the learning process may continue until all of the currently available training data 210 has been processed, or the learning process may be 'paused' after a given criteria is satisfied, to enable testing and potential release of the parameters 220 to the local CDS sites before all the training data 210 has been processed.

After the initial training is completed (or paused), the processor sets the learning system in a non-learning mode, wherein the parameters 220 remain fixed while each set of input data is processed by the learning system to produce a diagnosis 325 using these parameters 220. While in this non-learning mode, the processor 360 provides testing data 312, which comprises patient input data and a 'correct' diagnosis corresponding to this input data, to the learning system 320 and receives a corresponding output diagnosis from the learning system 320. This testing data 310 may be a subset of the training data 210 or it may be data 310 that has not been used to train the learning system.

The processor also receives the 'correct' diagnosis 315 from the training data 312 and compares these two diagnoses 315, 325 to determine the difference between these diagnoses 315, 325. The processor 315 assesses the differences for the sets of testing data and provides an accuracy report 358. If the operator of the global CDS system determines that the reported accuracy is sufficient, the operator may instruct the processor 360 to provide the parameters 210 to the network interface 340 for distribution to the local CDS systems. Otherwise, the parameters 210 are not released until further training data is processed, or the cause of the inaccuracy is otherwise determined.

In some embodiments, the testing and accuracy assessment is performed autonomously by the processor 350, wherein the processor 350 provides the new parameters 210 to the network interface for distribution based on whether the determined accuracy measures achieve pre-defined threshold values.

The example local CDS system of FIG. 3B also includes a learning system 320, a memory 330, a network interface 340, and a processor 360 that controls the operation of the learning system 320 and network interface 340. Although some of the components of the local CDS system of FIG. 3B have the same reference numeral as the components of the global CDS system of FIG. 3A, one of skill in the art will recognize that these like numbered components need not be identical to each other; they need only perform similar functions. The processor 360 of FIG. 3B is identified with a different reference numeral than the processor 350 of FIG. 3A to represent that they each perform a different control function.

When the network interface 340 receives the parameters 220 from the global CDS system, the processor 360 updates the current local training system parameters 120 based on these updated parameters 220.

As noted above, the processor 360 may be configured to test the updated parameters 220 using local testing data 312 before the local parameters 120 are replaced by these parameters 220, and may postpone the installation of the parameters 220 until the cause of the poor performance is determined.

With the updated parameters 220 now being the local parameters 120, the processor 360 may place the learning system 320 in a non-learning mode, preventing changes to these parameters 120. While in this non-learning mode, the local CDS system may be used to process new patient data (either a new patient or new data of an existing patient) 370 to provide a diagnostic output 325 using these updated local parameters 120. The processor 360 uses this diagnostic output 325 to create one or more diagnostic reports 368.

If it is subsequently discovered that a 'correct' diagnosis may be associated with a given set of new patient data 370, this diagnosis is added to the patient's input data to form new training and/or testing data. Optionally, the processor 360 may place the learning system 320 into the learning mode to process this training data and update the local parameters 120 based on this training data. Alternatively, the processor 360 may be configured to merely provide this new training data to the global CDS system and wait until it receives the next update of the parameters 220 from the global CDS system.

Periodically or aperiodically, the processor 360 directs the network interface 340 to retrieve new training data 110 from the memory 330 for transmission to the global CDS system for subsequent training of the global learning system 320 as detailed above. This transmission may occur as each new set of training data is created or when a given number of new sets of training data are created. The transmissions may also occur based on a schedule, or based on a request from the global CDS system, or based on a command from the operator of the local CDS system. Other triggers for initiating these transmissions will be evident to one of skill in the art.

As the global CDS system receives and processes the new training data 110 from the local CDS systems, it uses some or all of this new training data 110 to update the global learning system parameters 220 and provides these new parameters 220 to the local CDS system, initiating a repeat of the above process.

Figure 4:
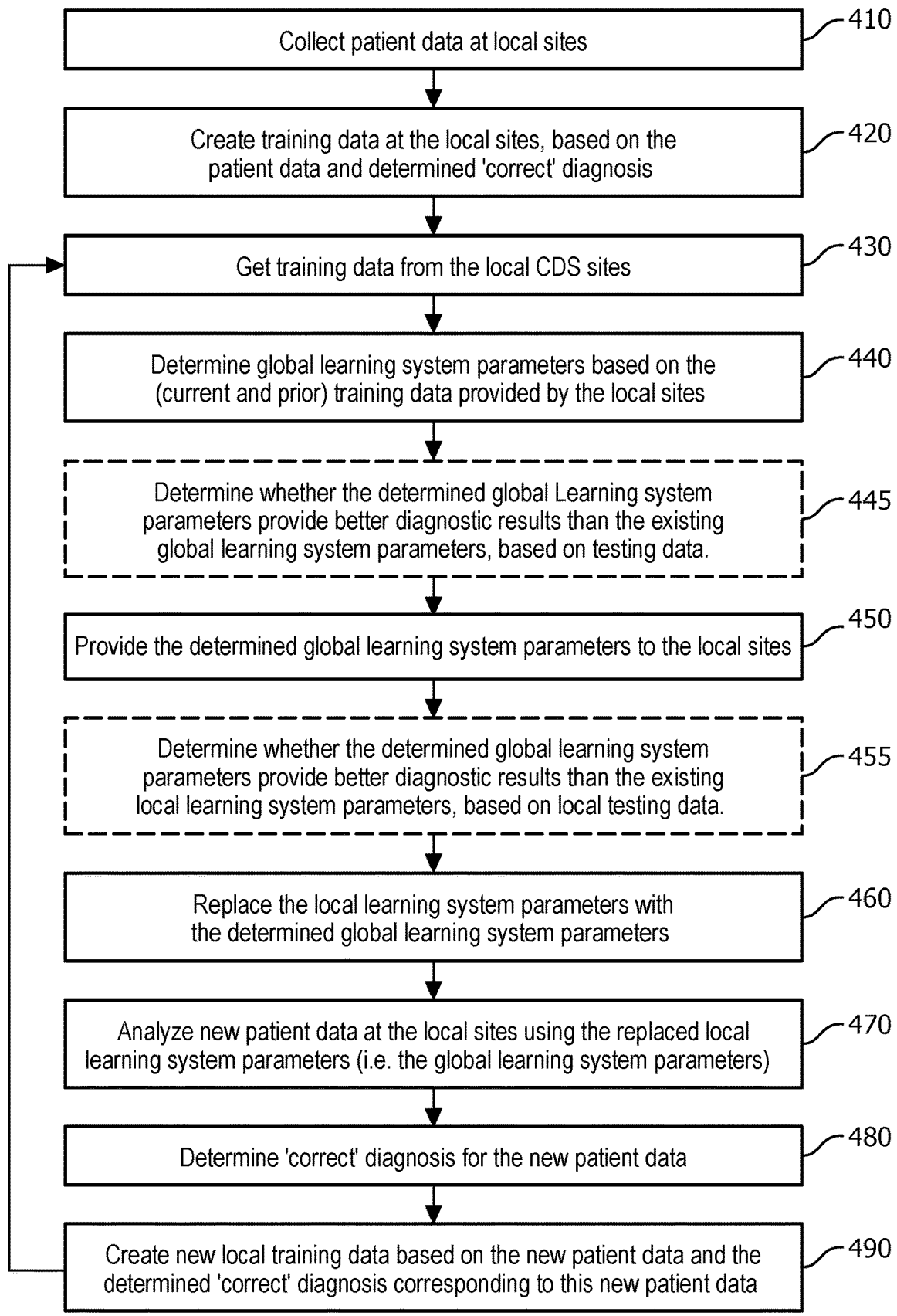
FIG. 4 illustrates an example flow diagram for communications among a network of clinical diagnostic support systems.

FIG. 4 illustrates an example flow diagram for communications among a network of clinical diagnostic support systems.

At 410, the local CDS systems collect sets of patient data, and, for those sets for which a 'correct' diagnosis can be determined, training data is created, at 420. As indicated by the loop 410-420, this is generally a continuing process over time. Optionally, this training data may be used to train the local CDS system.

The local training data is communicated to the global CDS system, at 430. The global CDS system uses some or all of this training data (some of the training data may be used to test the global CDS system) to train the global CDS system to determine a set of global learning system parameters based on this training data, at 440. Optionally, the performance of the global CDS system using these parameters may be assessed using testing data, at 445.

The determined global learning system parameters are provided to the local CDS systems, at 450, to update the local learning system parameters, at 460. A local CDS system may optionally assess the performance of its CDS systems using these global parameters, at 455, before replacing its local parameters.

Thereafter, new patient data is processed by the local CDS systems using the updated parameters from the global CDS system, at 480. If a 'correct' diagnosis can be provided for a new set of patient data, the local CDS system may create new training data, at 490, and submit it to the global CDS system, at 430. As indicated by the loop 430-490, this updating of training data and learning system parameters continues over time.

By providing a global CDS system that receives local training data from a plurality of local CDS systems, the quality and reliability of the expert systems at each CDS system can be expected to increase substantially, and this substantial increase in quality and reliability is provided with minimal burden placed on the local CDS systems.

Additionally, because the global CDS system has access to this large amount of patient data with accompanying 'correct' diagnoses, the global CDS system is able to perform other analyses that may further improve the diagnostic abilities of the local CDS systems. For example, it is often difficult to ascertain which elements of the set of patient data are most effective for providing a proper diagnosis, and/or whether pre-processing of the input data (such as forming ratios) would provide for better diagnoses. The global CDS system may be configured to apply analyses of the provided training data to address these issues, and others.

For example, the global CDS system may apply the training data to a genetic algorithm process that compares the performance of different configurations of the learning system, each configuration using a different set of elements used as input to the learning system. The different sets of elements may be generated by a genetic algorithm that combines elements that performed well in prior configurations.

When a new learning system configuration is identified as being superior to the current learning system configuration at the local CDS systems, this new system configuration may be provided to the local CDS system for use thereafter.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein the global CDS system also operates as a local CDS system and provides patient data and accompanying 'correct' diagnoses to the pool of patient data and diagnoses that is used when this CDS system operates as the 'global' CDS system detailed above.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A clinical diagnostic support (CDS) network comprising:
   a plurality of local CDS systems, each local CDS system comprising: a local learning system that:
   receives patient data and provides a corresponding diagnostic output based on local learning system parameters,
   receives a corresponding locally determined correct diagnosis, wherein the locally determined correct diagnosis is determined by an assessor,
   applies training data to the local learning system to update the local learning system parameters based on a comparison of the diagnostic output of the local learning system and the corresponding locally determined correct diagnosis, the training data including the patient data and corresponding locally determined correct diagnosis; and
   a network interface that provides the training data of the local learning system to a global CDS system; and
   the global CDS system, wherein the global CDS system includes a global learning system that:
   receives the training data from the plurality of local CDS systems;
   applies the training data to the global learning system to produce global learning system parameters based on a comparison of the diagnostic outputs of the global learning system and the corresponding locally determined correct diagnoses, and
   provides the global learning system parameters to the plurality of local CDS systems;
   wherein one or more of the plurality of local CDS systems selectively update their local learning system parameters based on the global learning system parameters and provide subsequent diagnostic outputs based on these updated local learning system parameters.

2. The network of claim 1, wherein each of the local and global learning systems includes a neural network, and the learning system parameters include a bias associated with each node of the neural network, and a weight associated with each connection between the nodes.

3. The network of claim 1, wherein at least one of the local CDS systems determines whether to update the local learning system parameters based on the testing data applied to the local learning system using the global learning system parameters, and the determination whether to update the local learning system parameters is based on a comparison of each diagnostic output of the local learning system and the corresponding previously determined diagnosis using the global learning system parameters.

4. The network of claim 1, wherein the global CDS system determines whether to provide the global learning system parameters to the plurality of local CDS systems based on the testing data received from the local CDS systems and applied to the global learning system using the global learning system parameters, and the determination whether to provide the global learning system parameters to the plurality of local CDS systems is based on a comparison of each diagnostic output of the global learning system and the corresponding previously determined diagnosis.

5. The network of claim 1, wherein the global and local learning systems include a particular structure for processing the patient data, and the global CDS system also processes the training data to identify an alternative structure that is superior to the particular structure, based on a comparison of the diagnostic output of the global learning system having this alternative structure and the previously determined diagnoses associated with the training data, and provides this alternative structure to the plurality of local CDS systems.

6. The network of claim 1, wherein at least one local CDS system selects not to update their local learning system parameters based on the global learning system parameters, such that the local learning system parameters of the at least one local CDS system differ from the global learning system parameters until at least another subsequent update of the global learning system parameters.

7. A method comprising:
   determining local learning system parameters at each of a plurality of local clinical diagnostic support (CDS) systems by applying training data to learning systems at each local CDS system, wherein the locally determined correct diagnosis is determined by an assessor,
   wherein the training data comprises patient data and corresponding locally determined correct diagnoses at each local CDS system, and
   wherein the local learning system parameters at each of the local CDS systems are determined based on a comparison of the diagnostic outputs of a local learning system at the local CDS system and the corresponding locally determined correct diagnoses;
   communicating the training data from the plurality of local CDS systems to a global CDS system;
   applying, at the global CDS system, the training data to a global learning system to determine global learning system parameters based on a comparison of the diagnostic outputs of a global learning system at the global CDS system and the corresponding locally determined correct diagnoses;
   communicating the global learning system parameters to the plurality of local CDS systems; and
   selectively updating the local learning system parameters with the global learning system parameters based on a comparison of the diagnostic outputs of the local learning system using the global learning system parameters and the diagnostic outputs of the local learning system using the previously determined local learning system parameters.

8. The method of claim 7, wherein each of the local and global learning systems includes a neural network, and the learning system parameters include a bias associated with each node of the neural network, and a weight associated with each connection between the nodes.

9. The method of claim 7, wherein the global CDS system determines whether to provide the global learning system parameters to the plurality of local CDS systems based on the testing data received from the local CDS systems and applied to the global learning system using the global learning system parameters, and the determination whether to provide the global learning system parameters to the plurality of local CDS systems is based on a comparison of each diagnostic output of the global learning system and the corresponding previously determined diagnosis.

10. The method of claim 7, wherein each of the global and local learning systems includes a particular structure for processing the patient data, and the global CDS system also processes the training data to identify an alternative structure that is superior to the particular structure, based on a comparison of the diagnostic output of the global learning system having this alternative structure and the previously determined diagnoses associated with the training data, wherein the method comprises providing this alternative structure to the plurality of local CDS systems.

11. The method of claim 7, wherein at least one local CDS system selects not to update their local learning system parameters based on the global learning system parameters, such that the local learning system parameters of the at least one local CDS system differ from the global learning system parameters until at least another subsequent update of the global learning system parameters.

\* \* \* \* \*